United States Patent [19]
Gaba et al.

[11] Patent Number: 5,918,762
[45] Date of Patent: Jul. 6, 1999

[54] CONTAINER INSTALLING SYSTEM

[75] Inventors: Rodolfo Gaba, Simi Valley; Michael Griffin, Agua Dulce, both of Calif.; Ignaty Gusakov, East Aurora, N.Y.; Ruane S. Jeter, Los Angeles; Gordon H. Marsh, West Hills, both of Calif.

[73] Assignee: Graphic Controls Corporation, Buffalo, N.Y.

[21] Appl. No.: 09/087,456

[22] Filed: May 28, 1998

[51] Int. Cl.[6] .................................................. B65D 25/22
[52] U.S. Cl. ..................... 220/751; 220/4.27; 220/23.83; 220/784; 220/481; 206/366; 206/1.5; 206/223
[58] Field of Search ............................ 206/1.5, 216, 223, 206/571, 366, 278, 501; 220/4.27, 23.83, 23.86, 4.01, 4.03, 4.26, 476, 480, 481, 23.87, 23.91, 527, 780, 784, 751

[56] References Cited

U.S. PATENT DOCUMENTS

| Re. 32,966 | 6/1989 | Miller et al. ........................... 220/23.86 |
|---|---|---|
| D. 307,841 | 5/1990 | Hanifl et al. . |
| D. 321,803 | 11/1991 | Dawson . |
| D. 335,373 | 5/1993 | Mosior . |
| 1,252,816 | 8/1918 | Kuehl . |
| 1,648,277 | 11/1927 | Korb . |
| 1,689,571 | 10/1928 | West . |
| 3,403,641 | 10/1968 | Baker . |
| 3,653,734 | 4/1972 | Ungaro . |
| 3,760,937 | 9/1973 | Van Wyngarden et al. . |
| 3,854,783 | 12/1974 | Teranishi . |
| 4,157,766 | 6/1979 | Gerdes ..................................... 220/784 |
| 4,227,758 | 10/1980 | Clare . |
| 4,366,915 | 1/1983 | Seidler ....................................... 206/1.5 |
| 4,572,368 | 2/1986 | Miller et al. ........................... 220/23.86 |
| 4,746,013 | 5/1988 | Suzuki et al. ............................... 206/1.5 |
| 4,809,850 | 3/1989 | Laible et al. . |
| 4,830,440 | 5/1989 | Burch . |
| 4,842,138 | 6/1989 | Sandel et al. . |
| 4,863,057 | 9/1989 | Hanifl et al. . |
| 4,946,057 | 8/1990 | Connolly et al. ........................ 220/481 |
| 4,988,003 | 1/1991 | Spitzer et al. . |
| 4,997,105 | 3/1991 | Fischer . |
| 5,058,764 | 10/1991 | Gaba . |

(List continued on next page.)

OTHER PUBLICATIONS

Sharps–A–Gator, Sharps Collection and Disposal System, Point–Of–Use Sharps Container, CA–4833–1, Devon Industries, Inc. (1992).

"Sharps Container System Product Profile," Sherwood Medical (1989).

"How To Use The In–Room Wall Enclosure System," Sage Products Inc. (1993).

"Serious About Infection Control? Look What's New From Sherwood!," Sherwood Medical (1989).

*Primary Examiner*—Stephen Castellano
*Attorney, Agent, or Firm*—Ratner & Prestia

[57] ABSTRACT

A secure installing system for mounting a container on a frame member, with ease of access to the container. The installing system is appropriate for use in a medical environment such as a hospital. The frame member may be a shelf bracket, or a cabinet for housing a medical waste container, and may be mounted to a wall. A container such as a glove box holder is installed on the frame member. The container may have a dispenser opening providing ready access to materials such as tissues or surgical gloves. The container is securely mounted to the frame member using a hook and snap arrangement and may be disengaged from the frame member in order to exchange stored materials such as tissues or surgical gloves. The hook and snap arrangement protect against accidental dislodging of the container from the frame member, thereby preventing possible contamination of stored materials. Frame members that are shelf brackets may support two containers each. Furthermore, shelf brackets may be joined and latched together in alignment for storage of multiple containers.

21 Claims, 13 Drawing Sheets

U.S. PATENT DOCUMENTS

| | | |
|---|---|---|
| 5,103,997 | 4/1992 | Shillington et al. . |
| 5,170,907 | 12/1992 | Sakai ................................... 220/481 |
| 5,178,322 | 1/1993 | Shillington . |
| 5,211,303 | 5/1993 | Mosior . |
| 5,287,980 | 2/1994 | Saltz . |
| 5,323,994 | 6/1994 | Shillington et al. . |
| 5,397,006 | 3/1995 | Terrell . |
| 5,399,005 | 3/1995 | Schafer . |
| 5,494,186 | 2/1996 | Marsh ................................... 220/481 |
| 5,516,001 | 5/1996 | Muckenfuhs et al. . |
| 5,544,751 | 8/1996 | Klodt et al. . |
| 5,588,541 | 12/1996 | Goetz . |
| 5,607,057 | 3/1997 | Eches et al. ......................... 220/4.27 |
| 5,671,856 | 9/1997 | Lisch ................................... 220/4.27 |

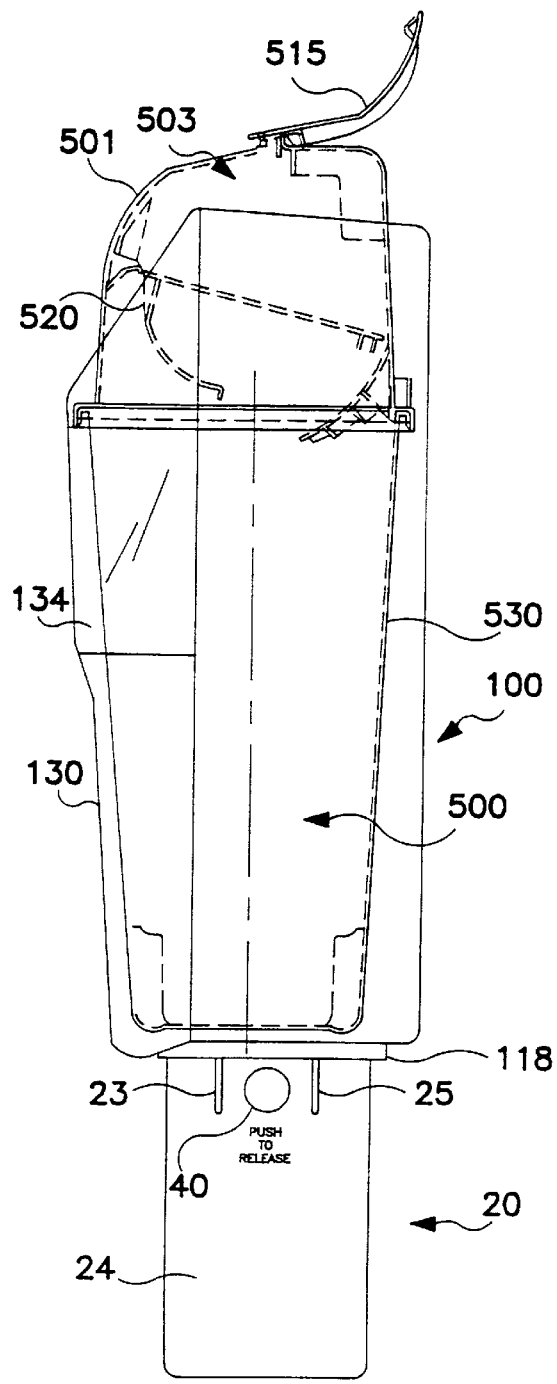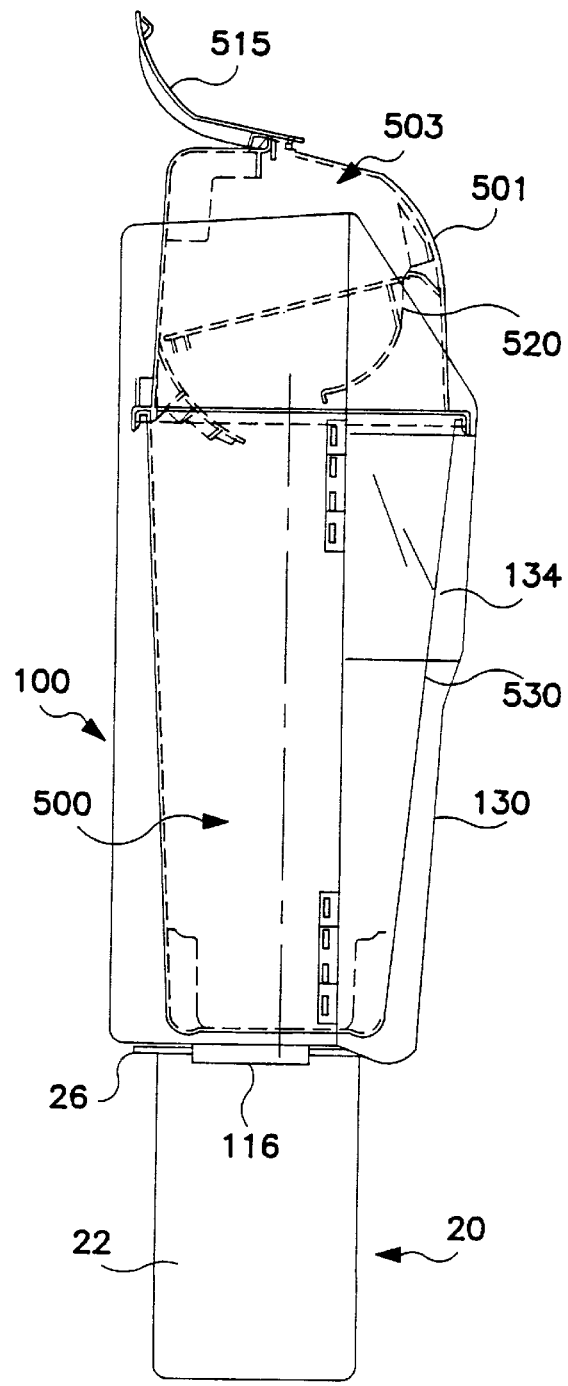
FIG. 7A
FIG. 7B

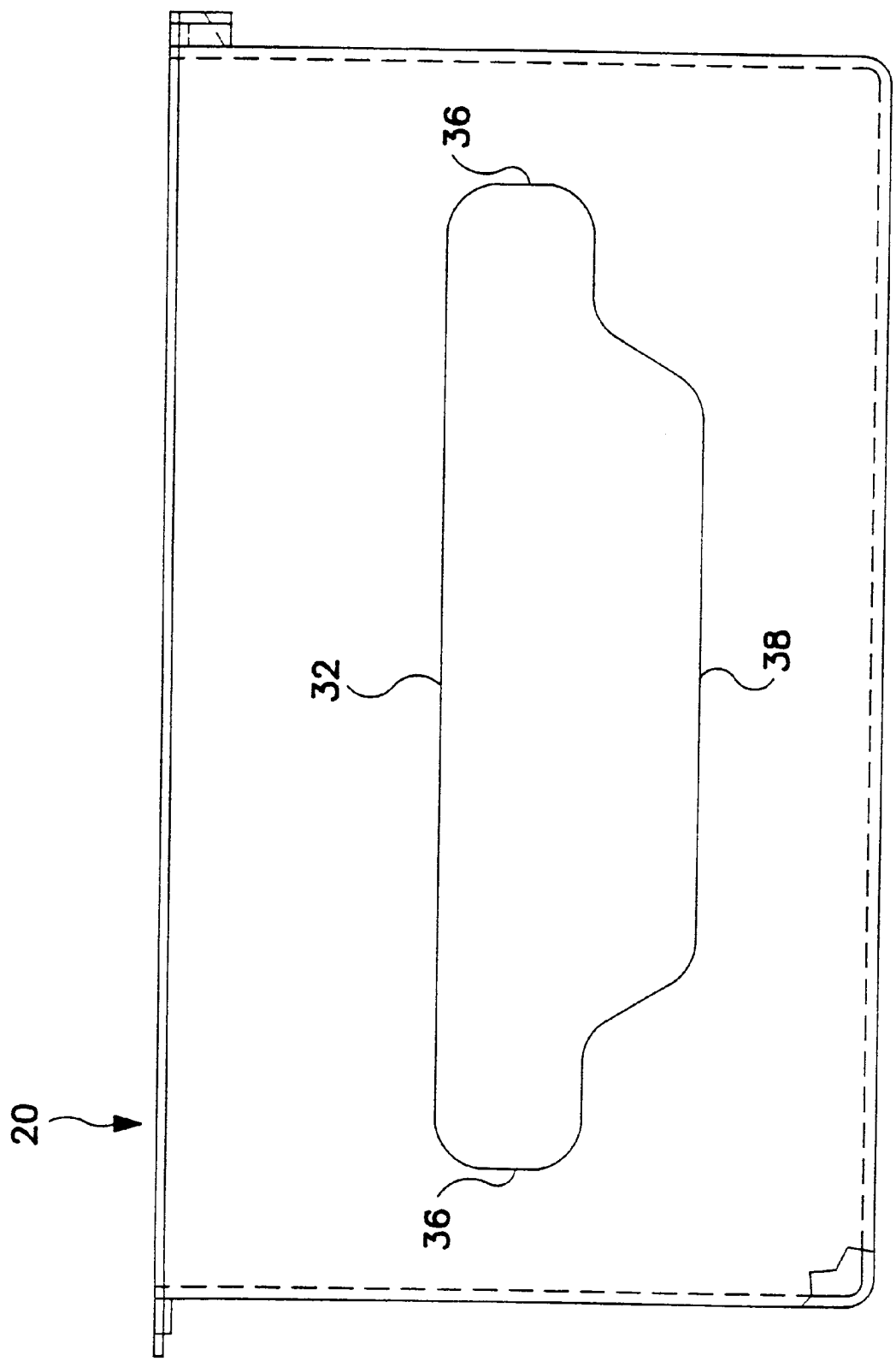

CONTAINER INSTALLING SYSTEM

FIELD OF THE INVENTION

The present invention relates to systems for mounting containers and, in particular, to systems for detachably mounting containers to frame members fixed to a vertical surface. Even more particularly, the present invention relates to a container system for dispensing items and for disposing of medical wastes.

BACKGROUND OF THE INVENTION

In many environments such as hospitals, clinics, and similar medical institutions, considerations of cleanliness are directly related to health concerns. The frequent use of disposable items, such as hypodermic needles, I.V. needles, razors, scalpel blades, tissues, and gloves, increases the need to guard against contamination. Once used, contaminated items can readily transmit disease. Hence, the proper handling, disposal, and dispensing of these types of items require particular care.

Various container systems for dispensing items and for disposing of medical wastes have been disclosed. One example of a secure container system composed of two containers, the second of which is mounted on the first such that the second can be laterally removed from the first when desired, is disclosed in U.S. Pat. No. 4,863,057, issued to Hanifl et al. For mounting of the second container on the first, the second container includes opposite flanges extending outwardly from opposite edges of the container. A pair of spaced, parallel channels are located on the first container, with each of the channels being shaped and located to accommodate one of the flanges of the second container. A stop is provided on the first container for selectively preventing removal of the second container from the first container, the stop being positioned in a first orientation to lock the second container in place and in a second orientation to unlock the second container to permit its removal. The first container includes a door oriented generally perpendicular to the mounting location of the second container on the first. The first container may comprise a cabinet for disposal of sharps, gloves, and other similar litter. The second container is slotted for dispensing of surgical gloves which, when used, may be discarded into the first container. This system does not provide, however, for access to the second container when the door of the first container is closed. When the door is closed and latched, the two containers are secured together and cannot be separated.

Another example of a secure container system composed of two containers, the second of which is mounted on the first such that the second can be laterally removed from the first when desired, is provided by U.S. Pat. No. 5,211,303, issued to Mosior. The system represents an improvement over the system disclosed by Hanifl et al. and includes a first container, a second container, flanges, and channels formed in a bracket. As for the Hanifl et al. system, when the flanges of the Mosior device are slid into the upper pair of channels of the bracket, the door of the first container must be open. When the flanges are slid into the lower pair of channels of the bracket, however, the door of the top container need not be open. The lower pair of channels allow access to the second container, regardless of whether the door of the top container is open. There is no stop preventing the second container from sliding away from the first container when the second container resides in the lower pair of channels. Thus, when a user pulls gloves, for example, out of a glove box (or second container) from a dispensing slot, the user is likely to exert a force on the glove box which may cause the glove box to slide unintentionally out of the lower pair of channels. This situation may prove problematic because the glove box must remain clean. If the glove box unintentionally slides out of channel and lands on the floor, there is the possibility that gloves located in the glove box may be so contaminated, because they fell on a dirty floor, that they may not be suitable for use in delicate medical situations. Detents temporarily hold the second container in place when installed in the lower channels. Such detents may have difficulty handling the stress of, for example, a hospital environment.

An example of a system for dispensing gloves is disclosed in U.S. Pat. No. 4,997,105 issued to Fischer. Fischer shows a glove box mounted to a wall-mounted stand. The mounting stand accommodates only a single glove box which rests on top of the stand. Moreover, this system may not provide sufficient ease in the detachment of the glove box.

U.S. Pat. No. 5,544,751 issued to Klodt et al. shows an apparatus for stacking storage containers. A plurality of trays may be attached to a box. Each tray includes mounting structure at the top and bottom of the tray, so that any one of the trays may be suspended from the box or from the bottom of another tray. Thus, any number of trays may be stacked and hung from the box. A latch is provided, at the top of each tray, in each of the four corners. A rib is provided at the bottom of each tray. A tab at the top of each tray engages the rib in the bottom of an upper tray or the box. Two biasing members are provided for pushing the tab against the rib, so as to maintain a secure attachment. Each tray can accommodate a drawer. The storage container stacking system of Klodt et al. may not be suitable for environments such as a hospital where ease of access to containers, ease of detachment of containers, and the need to guard against contamination are of primary concern. The system for mounting containers according to the present invention overcomes the limitations, difficulties, and shortcomings of these conventional devices by providing a secure system for detachably mounting a container to a frame member, with ease of access to the container.

SUMMARY OF THE INVENTION

The present invention provides a secure installing system for detachably mounting a container to a frame member while assuring ease of access to the container. The installing system comprises a frame member and a container. The frame member has a face, a hook disposed on the face, and a snap disposed on the face opposite the hook. The container has a perimeter, a first side with a top, a second side disposed opposite the first side with a top, a flange disposed around the perimeter and on the tops of the first and second sides, and a cantilever portion disposed in a portion of the flange adjacent to the second side. The flange has a step adjacent to the first side adapted to engage the hook of the frame member. The cantilever portion is adapted to engage the snap of the frame member. Engagement between the step of the flange and the hook of the frame member, and between the cantilever portion of the flange and the snap of the frame member, detachably mounts the container to the frame member.

BRIEF DESCRIPTION OF THE DRAWING

The invention is best understood from the following detailed description when read in connection with the accompanying drawing. It is emphasized that, according to common practice, the various dimensions of the installing system of the present invention as shown in the drawing are not necessarily to scale. On the contrary, the width or length and thickness of the various dimensions may be arbitrarily expanded or reduced for clarity.

FIG. 7A is a right-hand side view of the container mounted on the cabinet frame member, as illustrated in FIG. 6A, with a medical waste container inserted into the inner space of the cabinet;

FIG. 7B is a left-hand side view of the installing system illustrated in FIG. 7A;

FIG. 12 is a front view of a container with a T-shaped dispenser opening in accordance with an embodiment of the present invention.

DETAILED DESCRIPTION OF THE INVENTION

Figure 1:
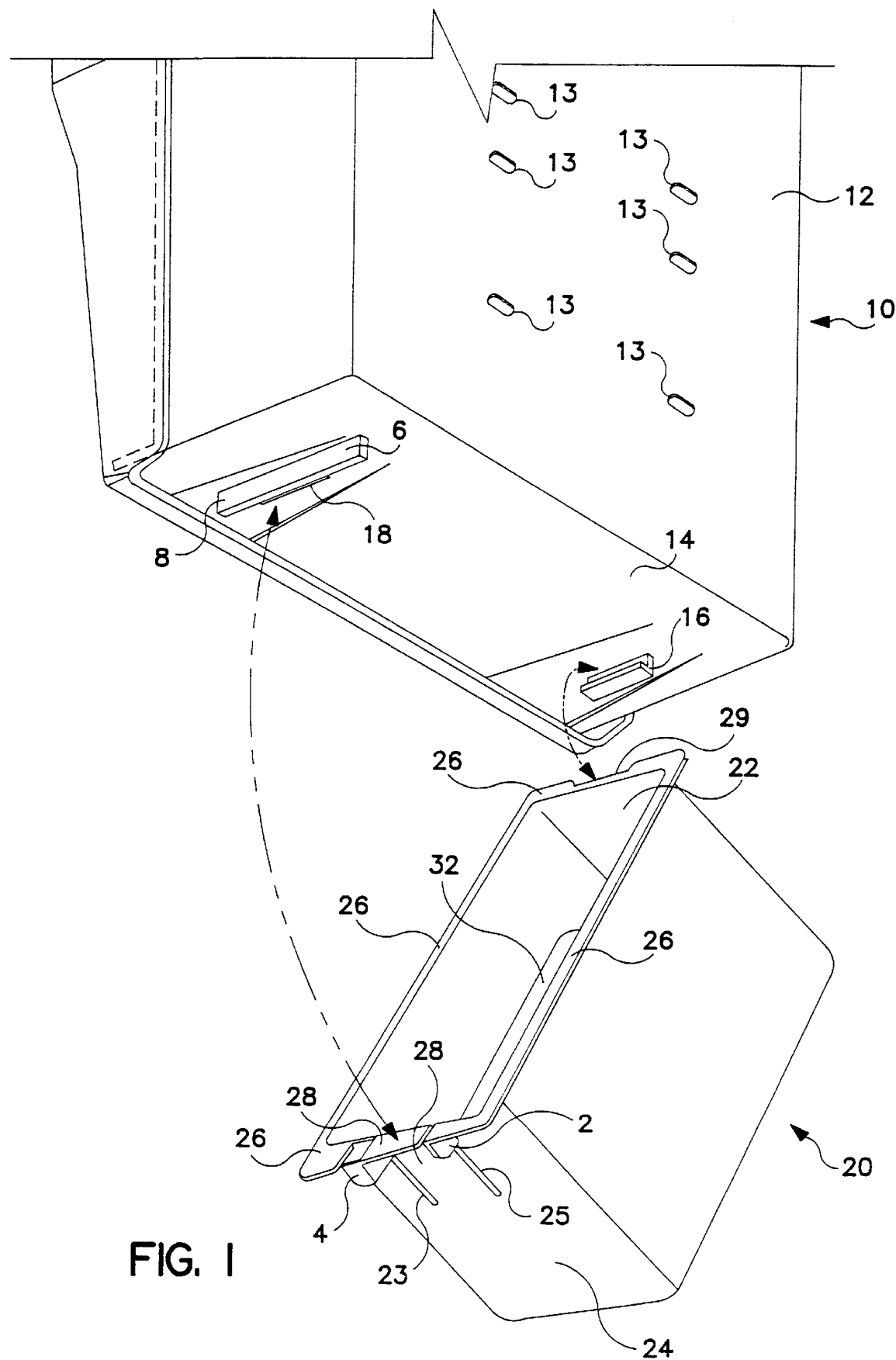
FIG. 1 illustrates an installing system for detachably mounting a container to a cabinet frame member in accordance with an embodiment of the present invention.

Referring now to the drawing, wherein like reference numerals refer to like elements throughout, FIG. 1 shows an installing system according to an embodiment of the present invention comprising a frame member 10 and a container 20. Frame member 10 has a face 14, a hook 16, and a snap 18. Hook 16 and snap 18 are either bonded to face 14 or are an integral, unitary part of face 14. Hook 16 and snap 18 are positioned on face 14 to facilitate the installation of container 20 on frame member 10. Reinforcing ribs 6 and 8 may be either bonded to snap 18 or formed as an integral, unitary part of snap 18. Ribs 6 and 8 are disposed on either side of snap 18 and extend the width of container 20. Thus, ribs 6 and 8 function, in addition to reinforcing snap 18, to prevent movement of container 20 once it has engaged frame member 10.

Container 20 has a perimeter, a first side 22 with a top, a second side 24 with a top, a flange 26, and a cantilever portion 28. Flange 26 is disposed around the perimeter and on the tops of first and second sides, 22 and 24, respectively. Flange 26 has a step 29 adjacent to first side 22. Step 29 is adapted to engage hook 16 of frame member 10 as indicated by the shorter broken line in FIG. 1. Adjacent to second side 24, in a portion of flange 26, cantilever portion 28 is adapted to engage snap 18 of frame member 10 as indicated by the longer broken line in FIG. 1. Cantilever portion 28 of container 20 may be created by two vertically disposed slots 23 and 25 in second side 24 and flange 26 of container 20.

Projections may be provided on one or both of cantilever portion 28 and flange 26 adjacent cantilever portion 28. As illustrated in FIG. 1, a projection 2 is provided on flange 26 and a projection 4 is provided on cantilever portion 28. Projections 2 and 4 reinforce the respective components of which they form a part and facilitate manipulation by the user of container 20.

To install container 20 on frame member 10, the top of container 20 is pushed up against face 14 of frame member 10. Mounting and removal of container 20 may be achieved through vertically upward and downward motion, respectively. In particular, the top of first side 22 is pushed upward into engagement with hook 16 on face 14 of frame member 10. Step 29 in flange 26 adjacent first side 22 of container 20 engages hook 16 on frame member 10. Then second side 24 of container 20 is pushed upward to engage snap 18 of face 14 of frame member 10 as step 29 pivots within hook 16.

The user may apply pressure to cantilever portion 28 of second side 24 of container 20 to release container 20 from snap 18. Once snap 18 is disengaged and second side 24 of container 20 is lowered free of face 14, hook 16 may also be disengaged from container 20 by a downward pulling motion. Frame member 10 may have mounting holes 13 in a rear 12 to secure rear 12 to a vertical surface such as a wall. Container 20 is secured to frame member 10 and need not be secured to the vertical surface. The engagement between hook 16 and step 29, and between snap 18 and cantilever portion 28, secures container 20 to frame member 10 without regard to the position of any door or other component provided in frame member 10. Moreover, the engagement "locks" container 20 to frame member 10 and prevents any movement (such as a sliding movement) between those components.

Figure 2:
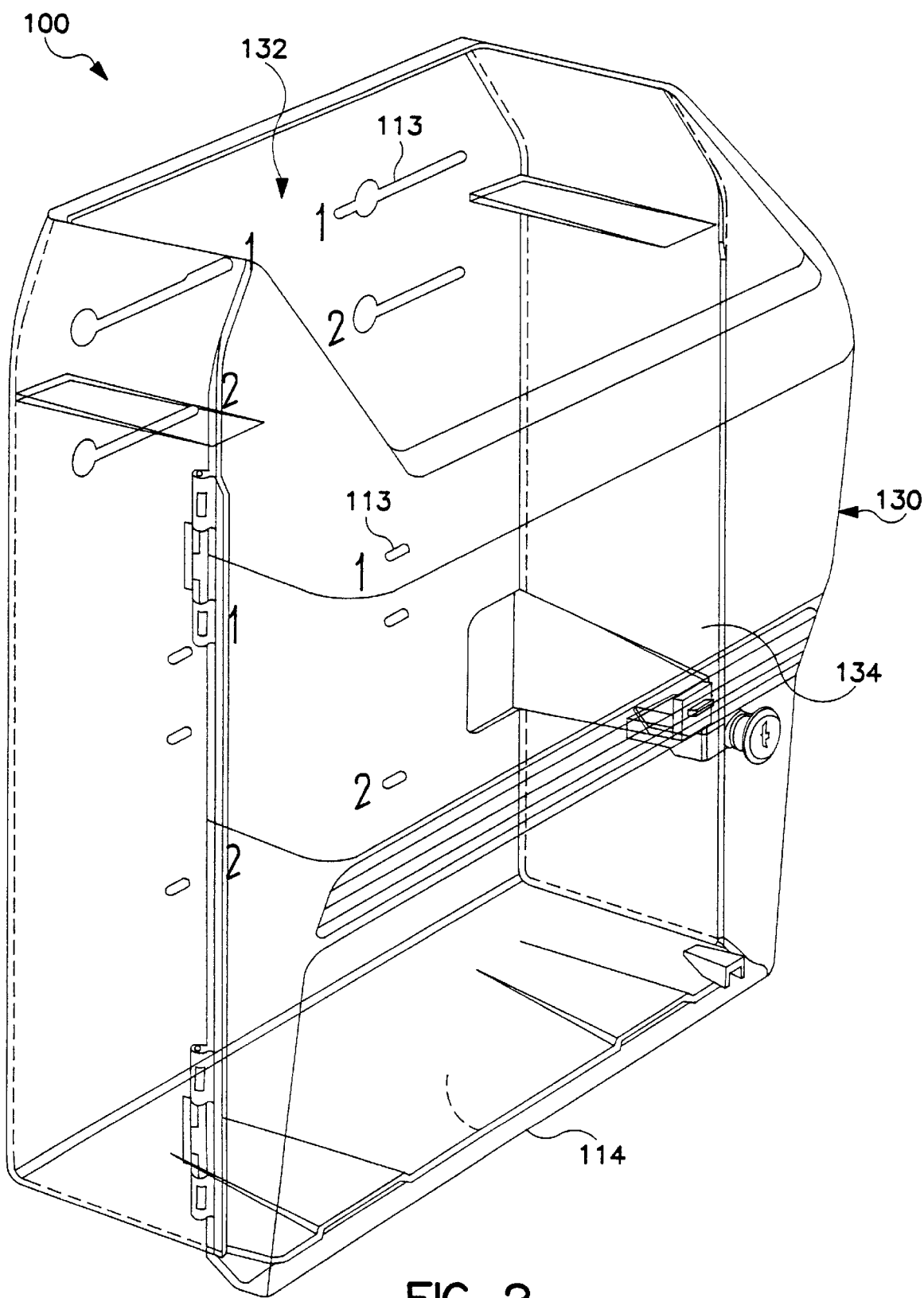
FIG. 2 is a front, left-hand side, and top perspective view of the frame member shown in FIG. 1.
Figure 3:
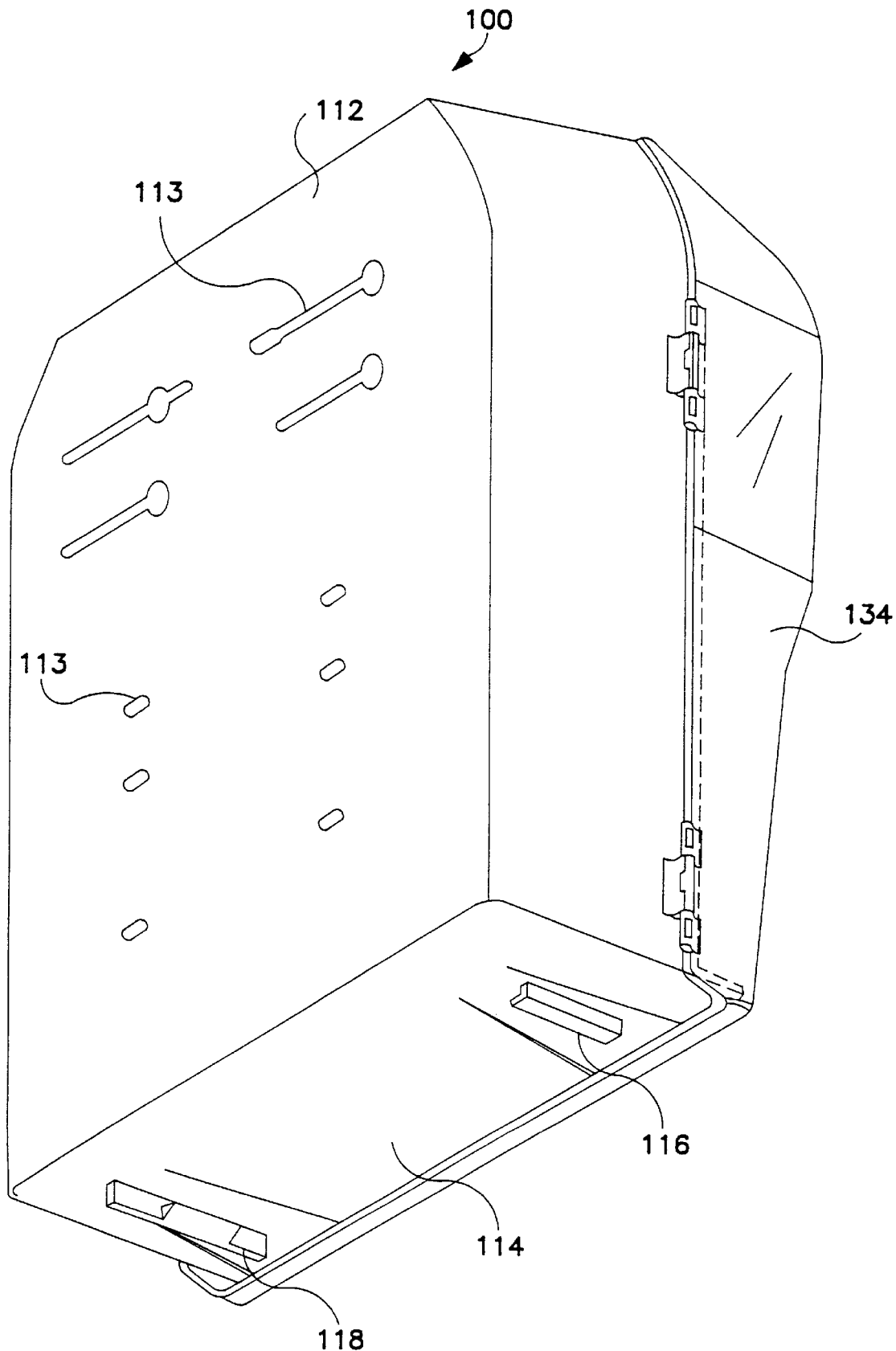
FIG. 3 is a rear, left-hand side, and bottom perspective view of the frame member illustrated in FIGS. 1 and 2.
Figure 4:
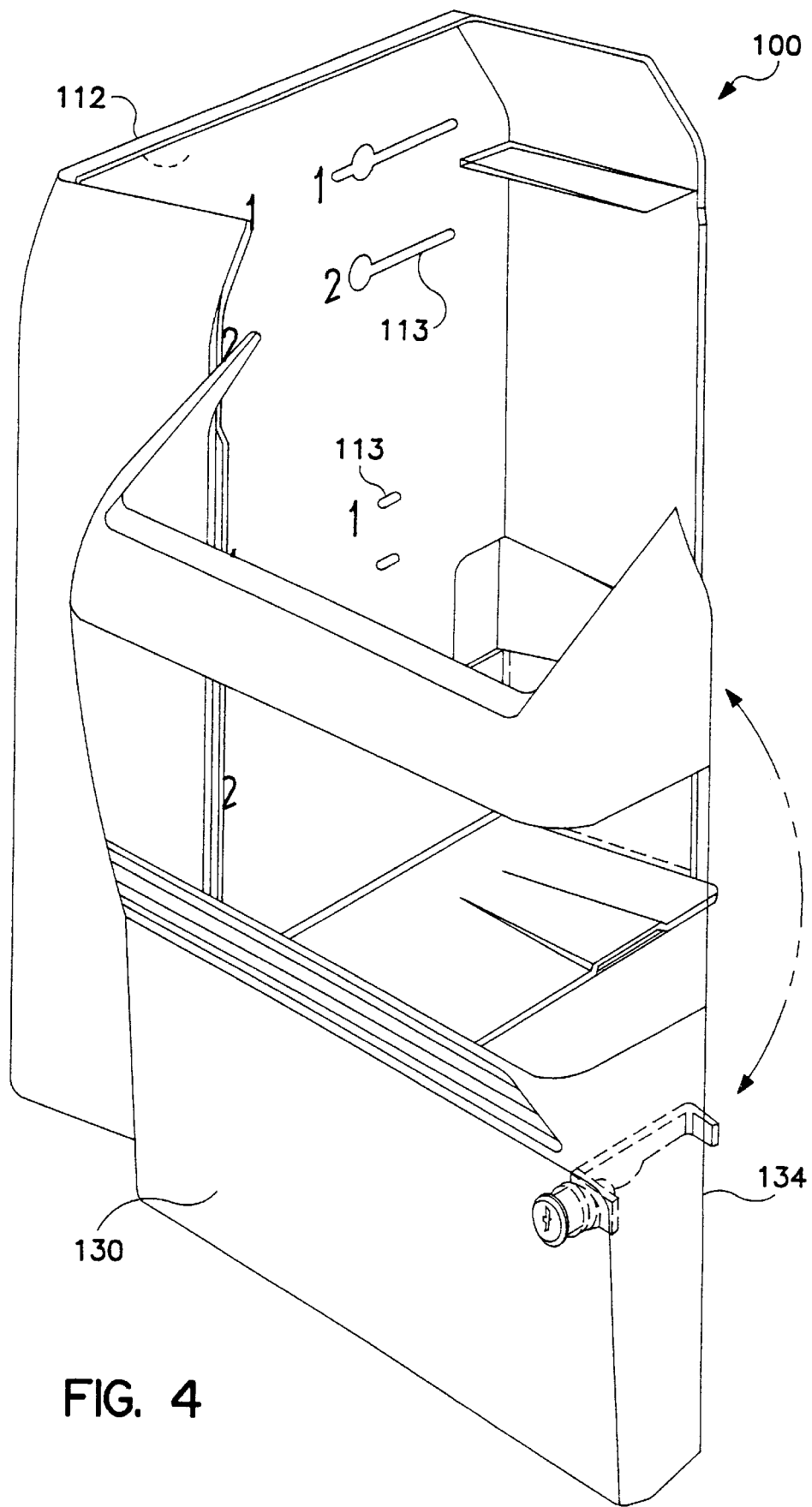
FIG. 4 is a perspective view of the frame member illustrated in FIGS. 1, 2, and 3, shown with the door open.

FIGS. 2, 3, and 4 illustrate a frame member that is a cabinet 100. Cabinet 100 has a front face 130, a bottom face 114, a door 134, a hook 116, and a snap 118. A door 134 is provided in front face 130 giving access to an interior space 132. Hook 116 and snap 118 are either bonded to face 114 or are an integral, unitary part of face 114. Hook 116 and snap 118 are positioned on face 114 to facilitate the installation of a container such as container 20 of FIG. 1. The mounting and removal of container 20, on and from cabinet 100, respectively, is as described above in connection with frame member 10. This configuration permits the user to install or remove container 20 from cabinet 100 without regard to whether door 134 of cabinet 100 is open or closed. In fact, a gap exists between the front of door 134 and the front of container 20; there is no contact at all between door 134 and container 20.

Cabinet 100 may have mounting holes 113, in a rear 112, adapted to receive fasteners such as screws and bolts.

Mounting holes 113 in rear 112 may be used to secure rear 112 to a vertical surface such as a wall. Indicia such as the numbers "1" and "2" may be provided adjacent to mounting holes 113 to facilitate securement.

Figure 5:
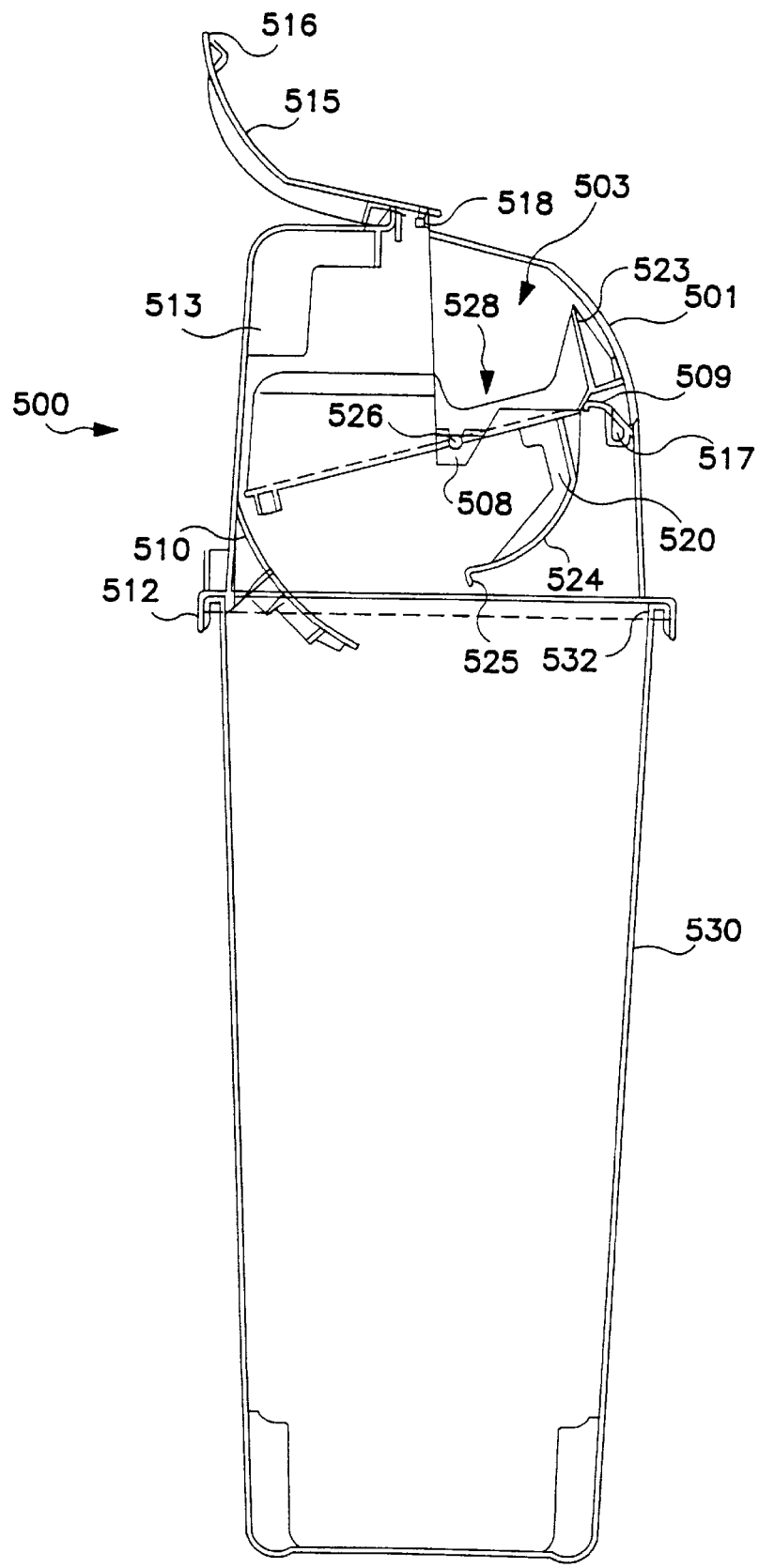
FIG. 5 shows a medical waste container that may be inserted into and removed from the cabinet frame member illustrated in FIGS. 14.

Interior space 132 to which access is given by door 134 may accommodate an inner container, such as a medical waste container 500 shown in FIG. 5. Medical waste container 500 may be inserted and removed, through door 134, into and from interior space 132 of cabinet 100. Medical waste container 500 has a hollow housing enclosure 501 and a hollow disposal container 530, which are attached to each other, and a closure or tumbler 520 pivotally mounted within housing enclosure 501. Housing enclosure 501 is provided with a flap or ramp 510 which extends beneath housing enclosure 501 and into disposal container 530 as shown. Disposal container 530 is preferably snap-fitted onto housing enclosure 501 in a conventional fashion as shown by lip 532 of disposal container 530 which is engaged by snap-tab 512 of housing enclosure 501. Other attachment mechanisms can be used as desired. Also shown in FIG. 5 are ribs 513 which reinforce the upper back interior portion of housing enclosure 501 and extend parallel to the cross-sectional plane of FIG. 5.

Tumbler 520 forms a barrier which restricts access by a user both to the interior of housing enclosure 501 and to the interior of disposal container 530 when tumbler 520 is rotated to dispose of a sharp (not shown) deposited in housing enclosure 501. To further secure medical waste container 500, lid 515 can be closed. Lid 515, which is shown in the open position, is pivotally mounted to housing enclosure 501 by hinge 518 and has locking tabs 516 which are configured to engage locking aperture 517 of housing enclosure 501. Upper opening 503 is provided in housing enclosure 501 to permit access to the interior of housing enclosure 501, when lid 515 is open, for depositing sharps or other medical waste products to be disposed. To provide for unimpeded rotation of tumbler 520, a chute 528 is defined to ensure that any sharps to be disposed do not become wedged during rotation of tumbler 520.

Tumbler 520 is pivotally mounted inside housing enclosure 501 by pivot pins 526 engaged in pivot brackets 508 formed on the interior of housing enclosure 501. Tumbler 520 includes an upper portion 523 and a curved lower portion 524 which are dimensioned so that together they extend across upper opening 503 of housing enclosure 501 when mounted and rotated in housing enclosure 501. Upper portion 523 and curved lower portion 524 may be used to prevent over-rotation of tumbler 520. Curved lower portion 524 has curvature sufficient to rotate within the curvature of housing enclosure 501 and also includes a flange 525 for engaging lower stop 509 of housing enclosure 501.

Figure 6A:
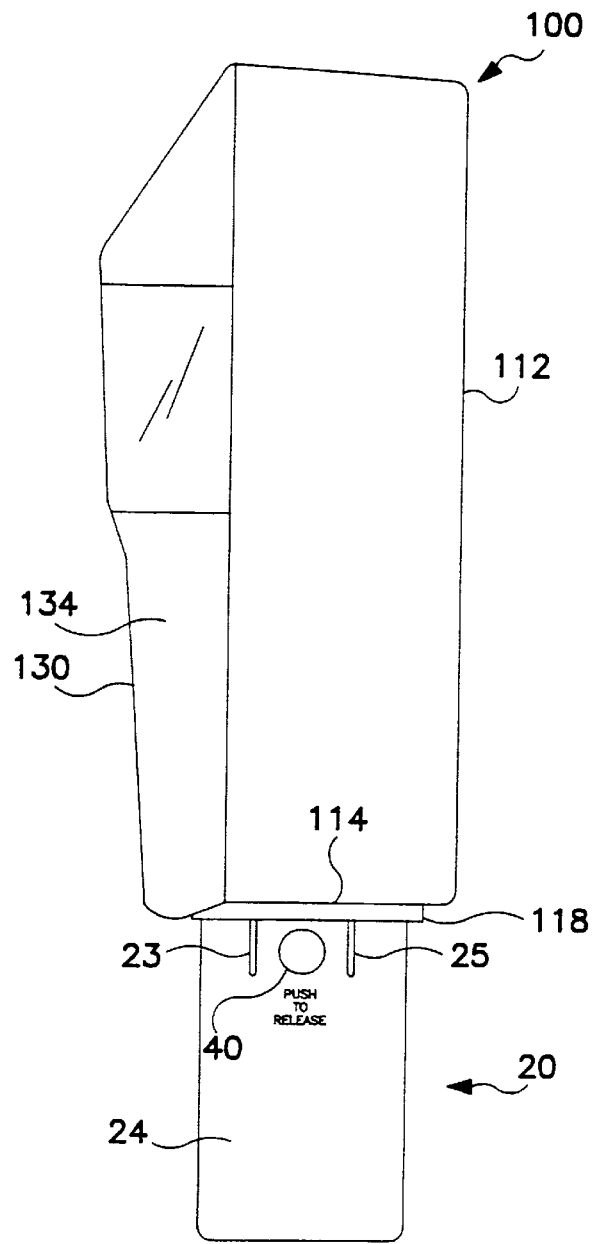
FIG. 6A is a right-hand side view of the container mounted on the cabinet frame member which were illustrated in a separated position in FIG. 1.
Figure 6B:
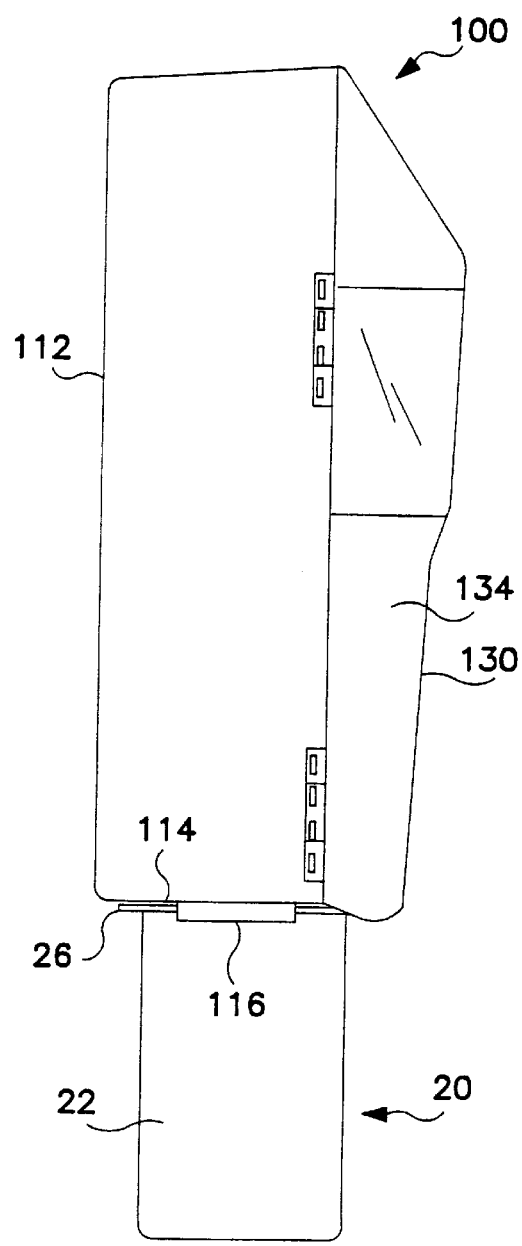
FIG. 6B is a left-hand side view of the installing system illustrated in FIG. 6A.

FIGS. 6A and 6B show side views of container 20 mounted on cabinet 100. Cantilever portion 28 of container 20 (see FIG. 1) is created by two vertically disposed slots 23 and 25 in second side 24 of container 20. Cantilever portion 28 may include a push button 40 adapted to release cantilever portion 28 from snap 118 of cabinet 100. Indicia such as "PUSH TO RELEASE" may be provided adjacent to push button 40 as instructions for the user.

FIGS. 7A and 7B also show side views of container 20 mounted on cabinet 100. FIGS. 7A and 7B show a medical waste container 500 inserted into interior space 132 of cabinet 100. Once door 134 is closed, medical waste container id 500 is fixed in place in interior space 132 of cabinet 100. Even with door 134 closed, however, access can still be gained to upper opening 503 of housing enclosure 501 of medical waste container 500. A portion of housing enclosure 501 is shown projecting upward out of cabinet 100. Moreover, the user may freely operate the lid 515, pivotally mounted to housing enclosure 501, even when door 134 is closed. Further, this configuration permits the user to install or remove container 20 from cabinet 100 without regard to whether door 134 of cabinet 100 is open or closed.

Figure 8:
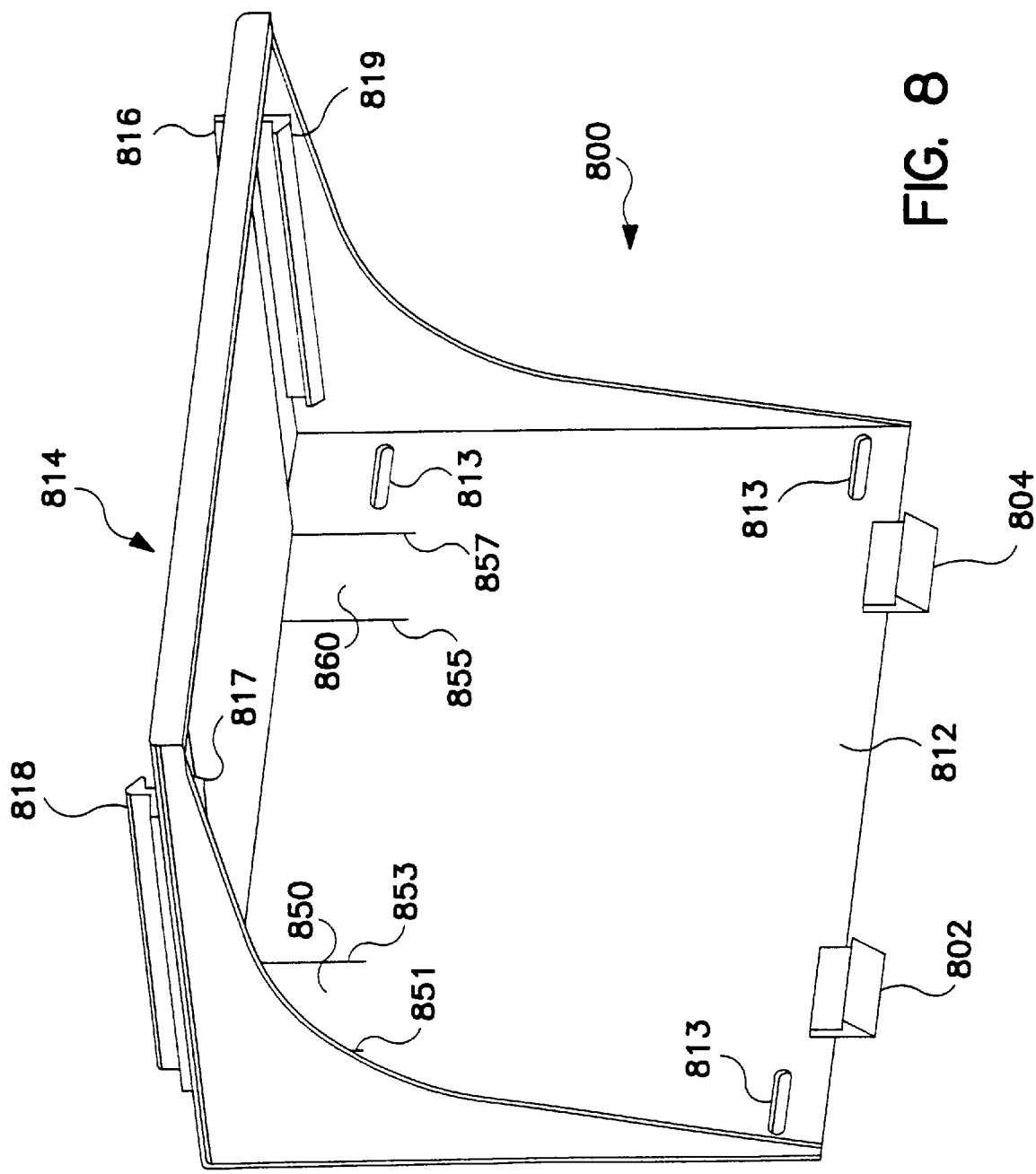
FIG. 8 is a perspective view showing the front and left-hand side of a frame member that is a shelf bracket in accordance with another embodiment of the present invention.
Figure 10:
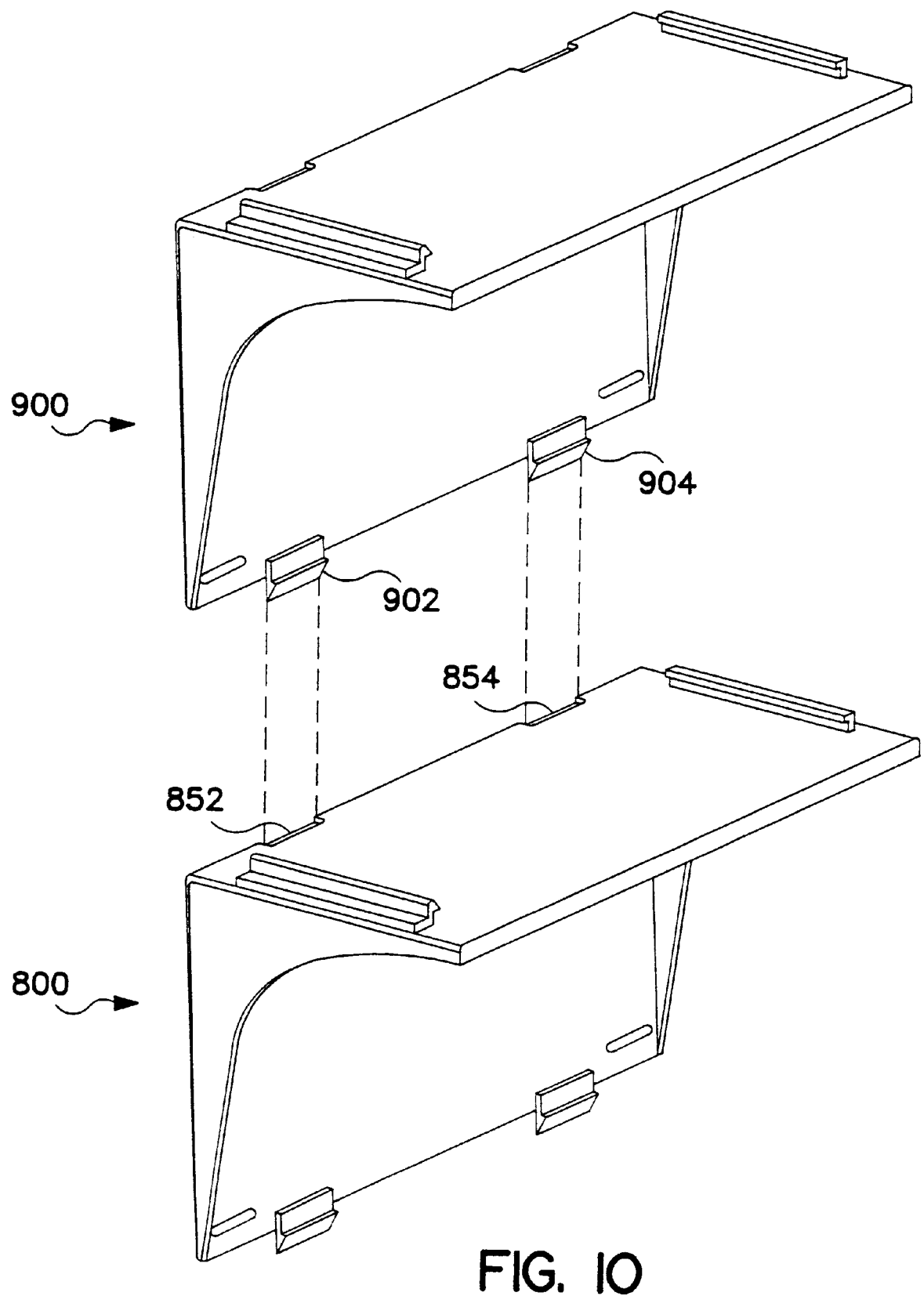
FIG. 10 shows a pair of shelf brackets, illustrated in FIGS. 8 and 9, as joined in cascade in accordance with an embodiment of the present invention.

FIG. 8 shows a frame member that is a shelf bracket 800 in an alternative embodiment of the present invention. Shelf bracket 800 has a rear 812, a flat 814 extending from rear 812, and latches 802 and 804 projecting from rear 812. Flat 814 includes openings 852 and 854, aligned with and adapted to receive latches 902 and 904 of an adjacent shelf bracket 900, as illustrated in FIG. 10. Thus, two or more shelf brackets, such as identical shelf brackets 800 and 900, may be joined in cascading fashion by reception of latches 902 and 904 in openings 852 and 854.

Figure 9:
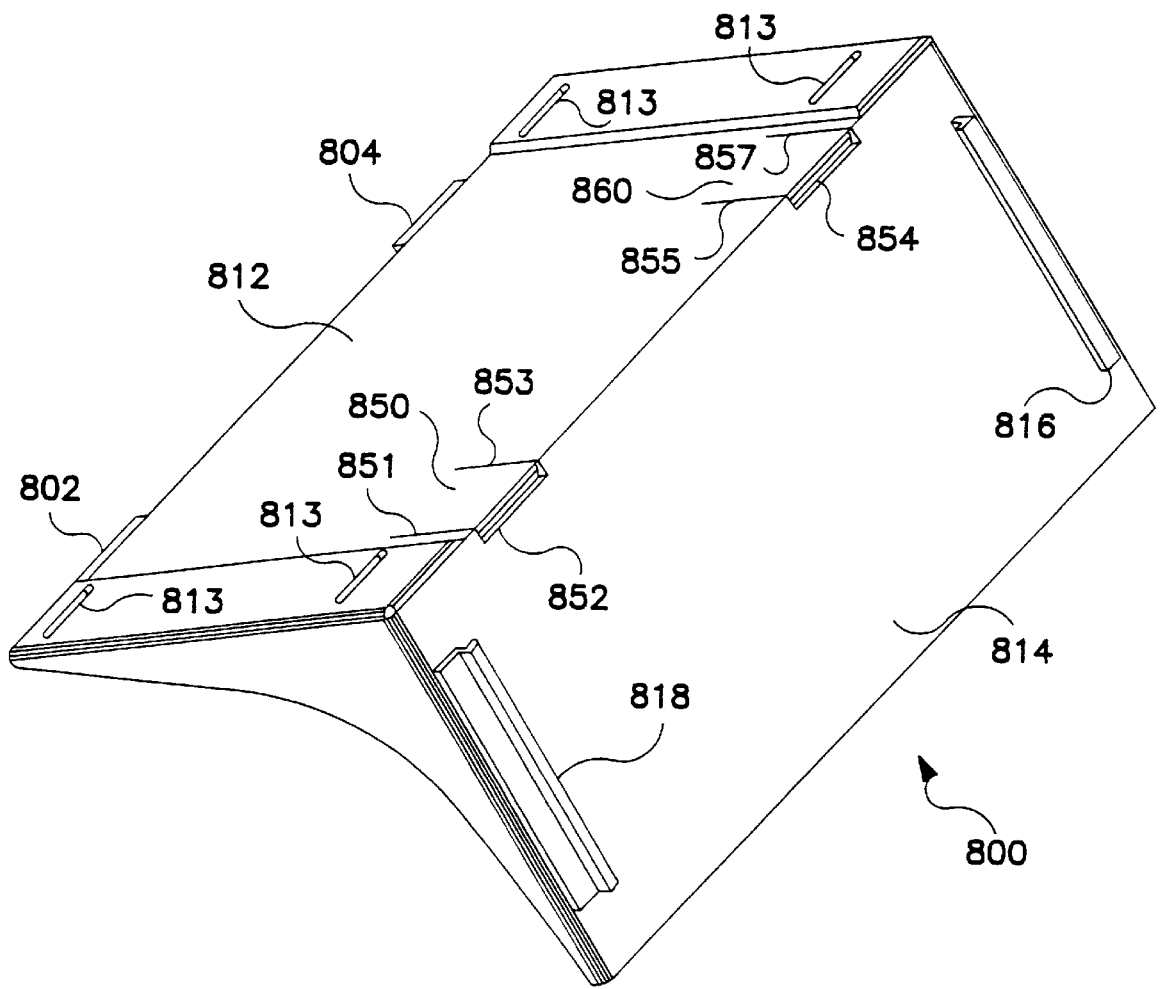
FIG. 9 is rear, left-hand side, and top perspective view of the frame member illustrated in FIG. 8.

Shelf bracket 800 further has a first snap 818 on top of flat 814, a first hook 816 positioned opposite first snap 818 on top of flat 814, a second hook 817 positioned underneath first snap 818 on the bottom of flat 814, a second snap 819 positioned underneath first hook 816 opposite second hook 817 on the bottom of flat 814. Mounting holes 813 in rear 812 may be used to secure rear 812 to a vertical surface such as a wall. Shelf bracket 800 also has latching cantilever portions 850, 860 (two are shown in FIGS. 8 and 9) provided in rear 812 and aligned with openings 852 and 854. Latching cantilever portion 850 is formed by vertical slots 851 and 853; latching cantilever portion 860 is formed by vertical slots 855 and 857.

Latching cantilever portions 850, 860 assist in locking in place latches 902 and 904 of adjacent shelf bracket 900 (see FIG. 10), and hence help to join and fix shelf bracket 800 to adjacent shelf bracket 900. Latching cantilever portions 850, 860 bend out of the way as latches 902 and 904 are pressed into engagement with openings 852 and 854. Latches 902 and 904 are held against flat 814 by the spring force of latching cantilever portions 850, 860 and the undercuts of latches 902 and 904 as they bear on flat 814.

Figure 11A:
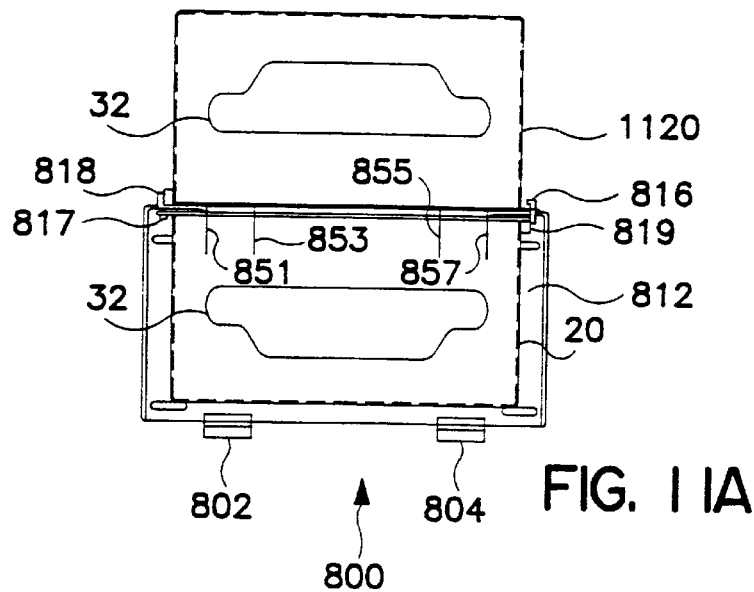
FIG. 11A is a front view of the shelf bracket illustrated in FIGS. 8 and 9, with a first container mounted upside down on top of the flat of the shelf bracket and an identical second container mounted upright on the bottom of the flat.
Figure 11B:
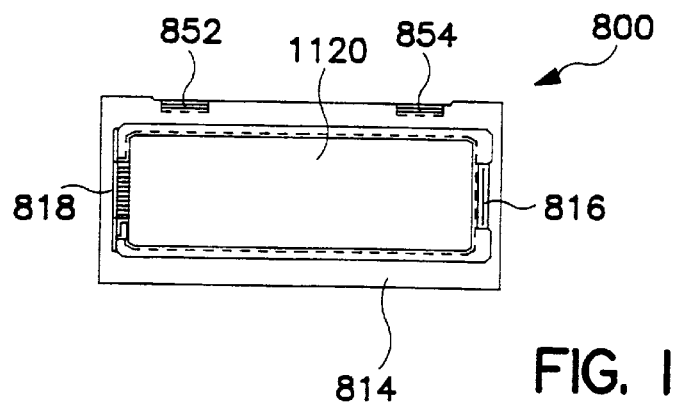
FIG. 11B is a top view of the system illustrated in FIG. 11A.
Figure 11C:
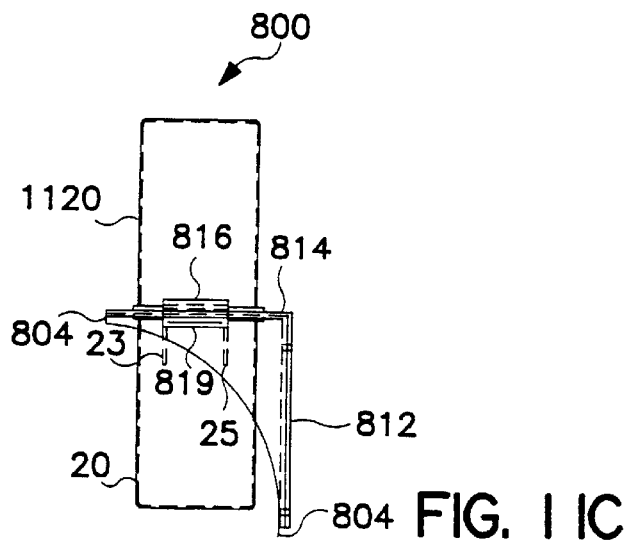
FIG. 11C is a side view of the system illustrated in FIGS. 11A and 11B.

One or two containers each having the same structure as container 20 of FIG. 1 may be installed on each shelf bracket 800, 900. FIG. 11A is a front view of shelf bracket 800 with container 20 mounted right-side up on the bottom of flat 814. A second container 1120, identical to container 20, is shown installed upside-down on the top of flat 814. Second container 1120 is mounted on the top of flat 814 by engagement of first hook 816 with step 29 and then of first snap 818 with cantilever portion 28, as described above. Container 20 is mounted on the bottom of flat 814 in the same manner by engaging second hook 817, and then second snap 819. FIG. 11B is a top view, corresponding to FIG. 11A, of shelf bracket 800 with second container 1120 mounted upside down on the top of flat 814, and identical container 20 installed on the bottom of flat 814. FIG. 11C is a side view, corresponding to FIG. 11A, of shelf bracket 800 with second container 1120 mounted upside down on the top of flat 814, and identical container 20 installed on the bottom of flat 814.

With two or more shelf brackets 800, 900 linked in a cascading fashion, multiple containers 20 (e.g., three or more) can be accommodated. The linking is achieved by snapping more than one shelf bracket 800 to an adjacent bracket 900. In such a configuration, only the top shelf bracket can accommodate two containers 20 while the rest accommodate one. By linking or snapping shelf brackets 800, 900 together, installation on a wall becomes easy because shelf brackets 800, 900 are held together and form a single unit. Mounting holes 813 in rear 812 of shelf bracket 800 accommodate mounting fasteners. By holding the bracket assembly against a wall, the shelf bracket 800 itself can be used as a template to locate the mounting positions of the fasteners. This process also assures consistent alignment of the cascaded shelf brackets 800, 900 relative to each other.

Container 20 (see FIG. 1) may include a dispenser opening 32 providing access, for example, to disposable items such as sharps, tissues, or gloves. In particular, access is given to disposable items through dispenser opening 32 when container 20 is mounted on frame member 10 such as, for example, cabinet 100 (see FIG. 2) or shelf bracket 800 (see FIG. 8). For example, container 20 may be a glove box holder shaped to accommodate a box of surgical gloves. FIG. 12 shows a front view of container 20 with a T-shaped dispenser opening 32 formed by a flattened extended oval portion 36 and a broad tail portion 38.

Another product that can be used with the shelf bracket assembly is a utility cabinet or container 20. Such a device would be installed in place of a glove is box holder. Utility container 20 could contain medical items such as face masks, face shields, resuscitation kits, gowns, and other assorted products frequently used in specific areas of a hospital. Such items could be packaged as kits and offered with utility container 20 to facilitate this storage. Such utility containers 20 may have doors for closure, draped openings, uncovered openings, or other configurations to suit the application.

Figure 13:
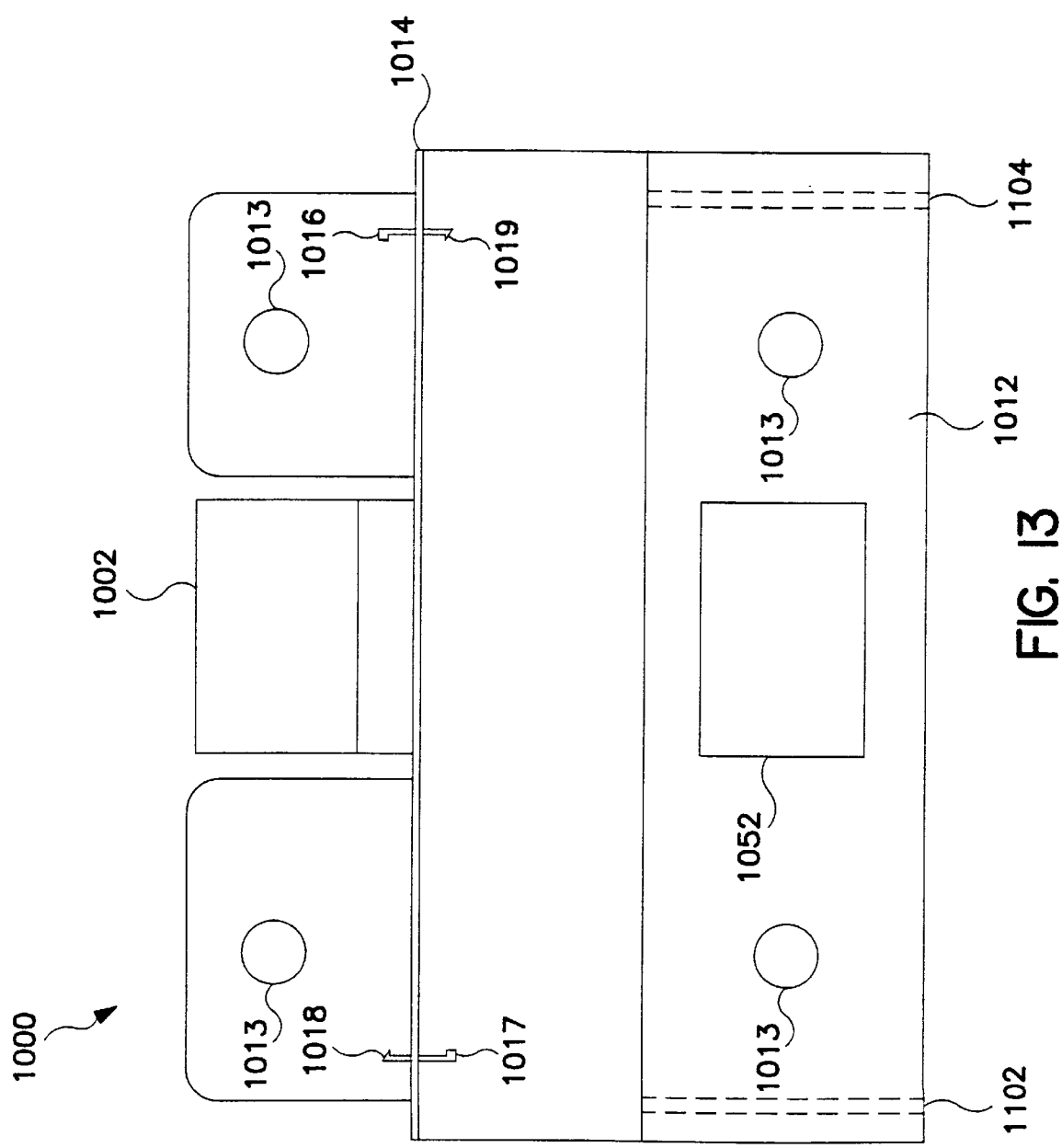
FIG. 13 is a front view of an alternative design for a shelf bracket in accordance with an embodiment of the present invention.

FIG. 13 is a front view of an alternative design for a shelf bracket in accordance with another embodiment of the present invention. Shelf bracket 1000 illustrated in FIG. 13 has a rear 1012, a flat 1014 extending from rear 1012, and a single latch 1002 projecting from rear 1012. Two or more shelf brackets, such as shelf bracket 1000, may be joined in cascading fashion. Rear 1012 includes an opening 1052, aligned with and adapted to receive a latch of an adjacent shelf bracket (not shown). Shelf bracket 1000 may further include aligning guides 1102 and 1104 for guiding and aligning a joining adjacent shelf bracket (not shown). Shelf bracket 1000 also has a first snap 1018 on top of flat 1014, a first hook 1016 positioned opposite first snap 1018 on top of flat 1014, a second hook 1017 positioned underneath first snap 1018 on the bottom of flat 1014, and a second snap 1019 positioned underneath first hook 1016 opposite second hook 1017 on the bottom of flat 1014. Mounting holes 1013 in rear 1012 may be used to secure rear 1012 to a vertical surface such as a wall.

One or two containers each having the same structure as container 20 of FIG. 1 may be installed on shelf bracket 1000. Container 20 may be mounted upside down on top of flat 1014. A second container, identical to container 20, may be installed on the bottom of flat 1014. Container 20 is mounted on the top of flat 1014 by engagement of first hook 1016 with step 29, and then of first snap 1018 with cantilever portion 28 as described above. A second, identical container 20 is mounted on the bottom of flat 1014 in the same manner by engaging second hook 1017, and then second snap 1019.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:
1. An installing system comprising:
    a frame member having:
        (a) a face,
        (b) a hook disposed on the face, and
        (c) a snap disposed on the face opposite the hook; and
    a container having:
        (a) a perimeter,
        (b) a first side with a top,
        (c) a second side with a top disposed opposite the first side,
        (d) a flange disposed around the perimeter and on the tops of the first and second sides, the flange having a step adjacent to the first side adapted to engage the hook of the frame member, and
        (e) a cantilever portion disposed in a portion of the flange adjacent to the second side, the cantilever portion adapted to engage the snap of the frame member;
    whereby engagement between the step of the flange and the hook of the frame member and between the cantilever portion of the flange and the snap of the frame member detachably mounts the container to the frame member.

2. The installing system according to claim 1, wherein the cantilever portion of the container is also disposed in a portion of the second side of the container and includes a push button adapted to release the cantilever portion from the snap of the frame member.

3. The installing system according to claim 1, wherein the cantilever portion of the container is created by two vertically disposed slots in the second side of the container.

4. The installing system according to claim 1, wherein the container further includes a T-shaped dispenser opening, formed by a flattened extended oval portion and a broad tail portion.

5. The installing system according to claim 1, wherein the frame member further has a rear with mounting holes adapted to secure the rear to a vertical surface.

6. The installing system according to claim 1, wherein the frame member is a shelf bracket and the container is a glove box holder.

7. The installing system according to claim 1, wherein the frame member is a cabinet and the container is a glove box holder.

8. A shelving system comprising:
    a plurality of shelf brackets, each of the shelf brackets having:
        (a) a rear,
        (b) a flat extending from the rear,
        (c) a latch projecting from the rear,
        (d) at least one of the rear and the flat including an opening aligned with and adapted to receive the latch of an adjacent shelf bracket of the plurality of shelf brackets, adjacent shelf brackets of the plurality of shelf brackets joined in cascading fashion by reception of the latch in the opening,
        (e) a hook disposed on the flat,
        (f) a snap disposed on the flat opposite the hook; and
    a container having:
        (a) a perimeter,
        (b) a first side with a top,
        (c) a second side with a top disposed opposite the first side,
        (d) a flange disposed around the perimeter and on the tops of the first and second sides, the flange having a step adjacent to the first side adapted to engage the hook of a shelf bracket, and
        (e) a cantilever portion disposed in a portion of the flange adjacent to the second side, the cantilever portion adapted to engage the snap of the shelf bracket;

whereby engagement between the step of the flange and the hook of the shelf bracket and between the cantilever portion of the flange and the snap of the shelf bracket detachably mounts the container to the shelf bracket.

9. The shelving system according to claim 8, wherein the cantilever portion of the container is also disposed in a portion of the second side of the container and includes a push button adapted to release the cantilever portion from the snap of the shelf bracket.

10. The shelving system according to claim 8, wherein the cantilever portion of the container is created by two vertically disposed slots in the second side of the container.

11. The shelving system according to claim 8, wherein the container further includes a front, and the front of the container is provided with a T-shaped dispenser opening formed by a flattened extended oval portion and a broad tail portion.

12. The shelving system according to claim 8, wherein the rear of each shelf bracket of the plurality of shelf brackets has mounting holes adapted to secure the rear to a vertical surface.

13. The shelving system according to claim 8, wherein the container is a glove box holder.

14. An installing system comprising:
   a cabinet having:
      (a) a front face,
      (b) a bottom face,
      (c) a door provided in the front face giving access to an interior space,
      (d) a hook disposed on the bottom face opposite the interior space,
      (e) a snap disposed on the bottom face opposite the hook and opposite the interior space; and
   a container having:
      (a) a perimeter,
      (b) a first side with a top,
      (c) a second side with a top disposed opposite the first side,
      (d) a flange disposed around the perimeter and on the tops of the first and second sides, the flange having a step adjacent to the first side adapted to engage the hook of the cabinet, and
      (e) a cantilever portion disposed in a portion of the flange adjacent to the second side, the cantilever portion adapted to engage the snap of the cabinet;
   whereby engagement between the step of the flange and the hook of the cabinet and between the cantilever portion of the flange and the snap of the cabinet detachably mounts the container to the cabinet.

15. The installing system according to claim 14, further comprising an inner container removably inserted through the door into the interior space of the cabinet.

16. The installing system according to claim 15, wherein the removable inner container is a medical waste container.

17. The installing system according to claim 14, wherein the cantilever portion of the container is also disposed in a portion of the second side of the container and includes a push button adapted to release the cantilever portion from the snap of the cabinet.

18. The installing system according to claim 14, wherein the cantilever portion of the container is created by two vertically disposed slots in the second side of the container.

19. The installing system according to claim 14, wherein the container further includes a front, and the front of the container is provided with a T-shaped dispenser opening formed by a flattened extended oval portion and a broad tail portion.

20. The installing system according to claim 14, wherein the cabinet further has a rear with mounting holes adapted to secure the rear to a vertical surface.

21. The installing system according to claim 14, wherein the container is a glove box holder.

\* \* \* \* \*